United States Patent
Storer

(10) Patent No.: US 6,217,583 B1
(45) Date of Patent: Apr. 17, 2001

(54) PROSTHETIC IMPLANT CEMENT DEFLECTOR SYSTEM

(75) Inventor: John Andrew Storer, Bayeux (FR)

(73) Assignee: Benoist Girard SAS (FR)

( * ) Notice: Subject to any disclaimer, the term of this patent is extended or adjusted under 35 U.S.C. 154(b) by 0 days.

(21) Appl. No.: 09/418,460

(22) Filed: Oct. 15, 1999

(30) Foreign Application Priority Data

Oct. 23, 1998 (GB) .................................................... 9823308

(51) Int. Cl.⁷ ............................................................ A61F 2/00
(52) U.S. Cl. ........................................................................ 606/92
(58) Field of Search .................................. 606/92, 93, 94; 623/908, 23.48

(56) References Cited

U.S. PATENT DOCUMENTS

| | | | |
|---|---|---|---|
| 5,092,892 | * | 3/1992 | Ashby .................................... 606/95 |
| 5,156,606 | * | 10/1992 | Chin ....................................... 606/86 |
| 5,192,283 | | 3/1993 | Ling et al. . |
| 5,385,566 | * | 1/1995 | Ullmark ................................. 606/95 |
| 5,425,768 | * | 6/1995 | Carpenter et al. ..................... 623/23 |
| 5,554,192 | * | 9/1996 | Crowninshield ....................... 623/22 |
| 5,658,351 | * | 8/1997 | Dudasik et al. ........................ 606/95 |
| 5,665,121 | | 9/1997 | Gie et al. . |
| 5,755,720 | * | 5/1998 | Mikhail ................................. 606/94 |
| 5,788,704 | | 8/1998 | Timperley . |
| 5,997,581 | * | 12/1999 | Khalili .................................. 606/92 |

\* cited by examiner

*Primary Examiner*—Gene Mancene
*Assistant Examiner*—Eduardo C. Robert
(74) *Attorney, Agent, or Firm*—Lerner, David, Littenberg, Krumholz & Mentlik, LLP

(57) ABSTRACT

A prosthetic implant cement deflector for use in prosthetic surgery used when employing a cannulated phantom prosthesis and/or prosthesis having a bore for utilizing a guide wire and provided with an insert portion. The cement deflector element is adapted to slide on a guide wire and has an external profile large enough to seal the interface distal tip between the guide wire and the surface of the distal end of the bore.

17 Claims, 3 Drawing Sheets

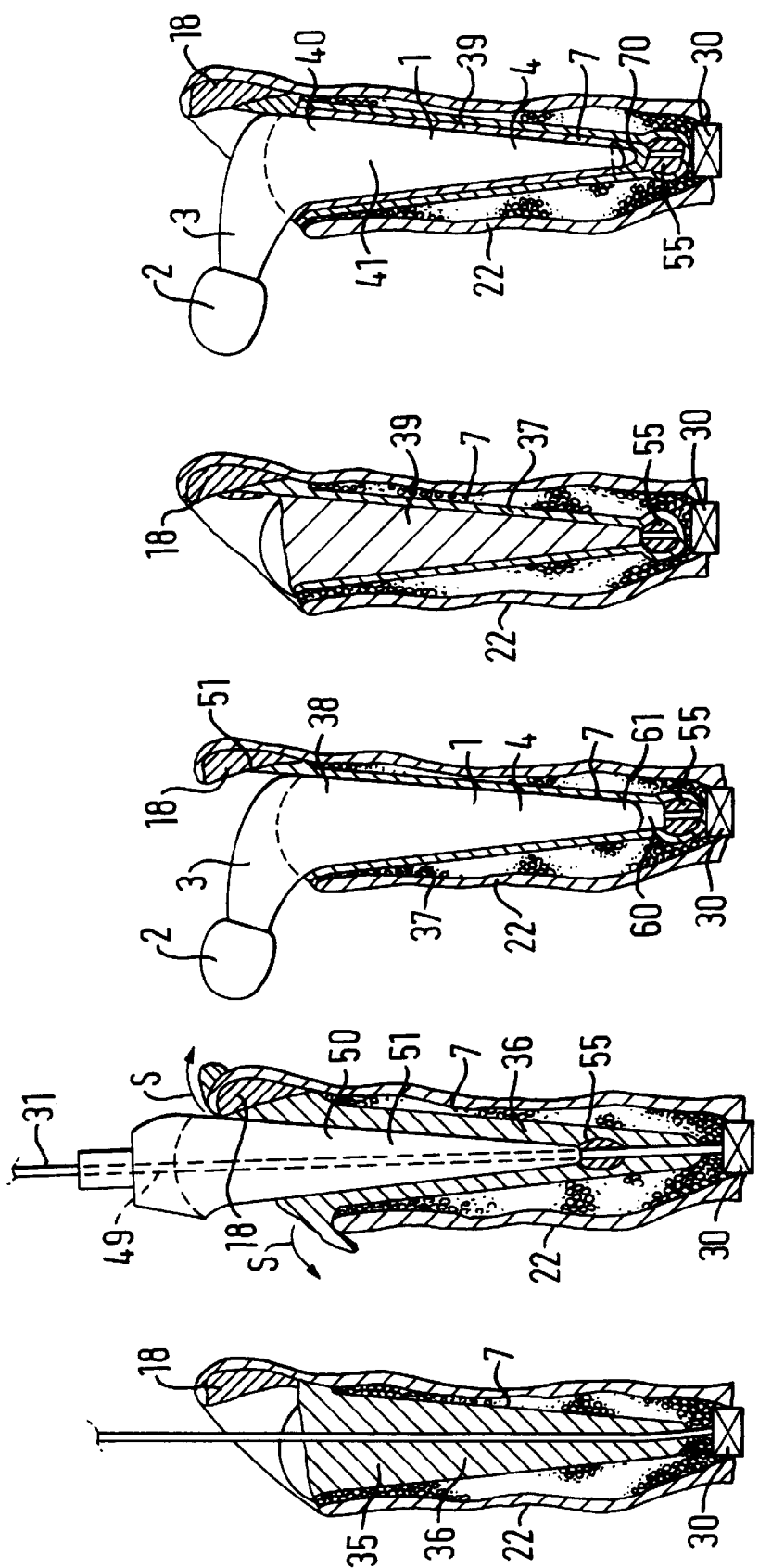

PROSTHETIC IMPLANT CEMENT DEFLECTOR SYSTEM

BACKGROUND OF THE INVENTION

1. Field of the Invention

This invention relates to a prosthetic implant cement deflector for use in prosthetic surgery when employing a cannulated phantom prosthesis and/or surgical prosthesis utilising a guide wire and provided with an insert portion.

2. Description of the Prior Art

U.S. Pat. No. 5,788,704 shows a method and apparatus for implanting a prosthesis. The invention relates to a method of guaranteeing the position and thickness of an adequate cement mantle around a cemented implant and shows the use of a phantom or trial component having a tapered insert portion. The phantom component is first inserted into a cavity which has been filled with bone chips which are compressed. A lining of cement is now applied to the cavity and a cannulated phantom is introduced into the opening.

The phantom is subsequently withdrawn from the cavity, the cement cavity inspected and the surgical prosthesis is finally implanted.

It has been found that using this technique there can sometimes be difficulties with the passage of cement into the bore of the phantom within the gap between the phantom and the guide wire. The present invention is intended to provide means for preventing this happening.

SUMMARY OF THE INVENTION

According to the present invention a prosthetic implant cement deflector for use in prosthetic surgery when employing a cannulated phantom prosthesis and/or prosthesis which has an insert portion and a bore adapted to receive a guide wire, comprising a cement deflector element adapted to slide on the guide wire and which can act to seal the interface between the guide wire and the surface of the distal end of the bore.

In a preferred embodiment the deflector element has an external profile which is greater than the external dimensions of the phantom or prosthesis with which it is to be used.

Thus, when in use, the deflection element is fitted to the guide wire before the phantom or surgical prosthesis and pushed down the wire in front of it. As the prosthesis approaches the distal end of the lined cavity the cement deflector pushes the cement aside and forms a recess at the distal end when the prosthesis is in its inserted position.

If desired, the cement of the deflector could also be used with the direct implantation of a surgical prosthesis along a guide wire, again being employed to prevent cement entering the bore and, if desired, to provide a void to allow the prosthesis to sink further. Preferably the element is adapted to be secured to the distal tip and it may be adapted to engage over at least part of the distal tip.

The deflector element can thus be formed with a recess which is adapted to receive the distal end of a prosthesis with which it is to be used, the recess being dimensioned to extend beyond the end of the prosthesis to provide a void to the stem tip.

The element can be made from any convenient material, for example synthetic plastics material in the form of polymethylmethacrylate (PMMA).

BRIEF DESCRIPTION OF THE DRAWINGS

The invention can be performed in various ways and some embodiment will now be described by way of example and with reference to the accompanying drawings in which:

FIGS. 2 to 10 are part cross-sectional side elevations showing how a hip prosthesis of the kind shown in FIG. 1 can come loose and be replaced by the method described in U.S. Pat. No. 5,788,704 and employing the present invention;

DESCRIPTION OF THE PREFERRED EMBODIMENTS

Figure 1:
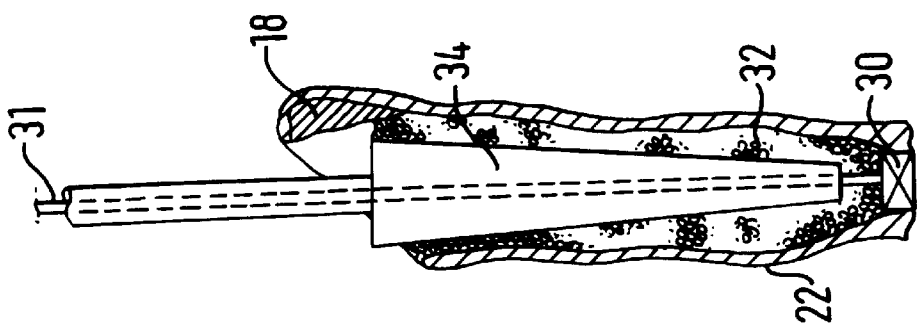
FIG. 1 is a diagrammatic cross-section showing installation of a total hip prosthesis of known kind in a femur.

FIG. 1 shows an idealised primary hip intramedullary femoral prosthesis 1 of the straight tapering collarless polished design concept located in a femur 15. The prosthesis has a head 2, neck 3 and stem 4 and is held in place by bone cement indicated by reference numeral 16. The cortical bone 17 of the femur 15 retains some cancellous bone 18. The stem 4 is centralised in the canal by a centraliser 19 of known type and the canal is plugged by a bone plug 20.

Figure 2:
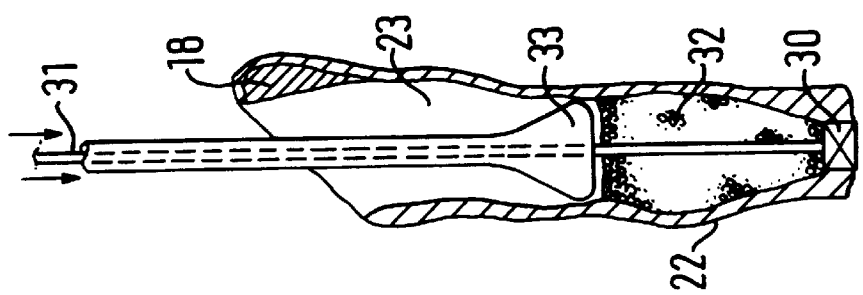

FIG. 2 illustrates what can happen when an implant, as shown in FIG. 1, fails. The stem 4 together with the cement 16 break away from the bone and a pendulum effect is produced as shown by arrows 21. This causes severe damage within the bone so that all that is left is a thin cortex 22. A space 23 is created which becomes filled by fluids and fibrous tissues.

Figure 3:
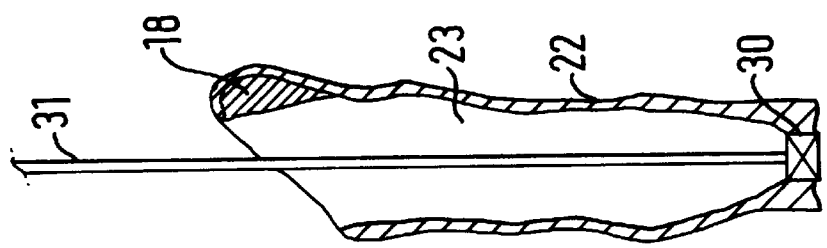
Figure 4:
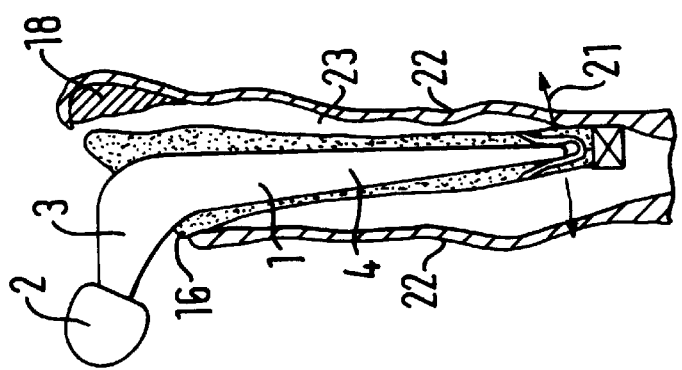
Figure 5:
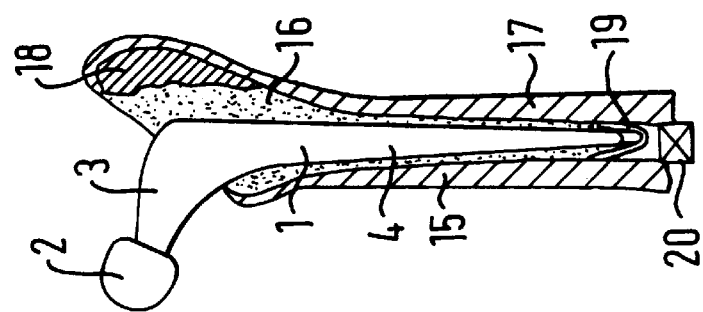

U.S. Pat. No. 5,665,121 shows an implant and a method by which the damaged joint can be repaired and this method will now be described further showing how it can be used in the present invention. The revision procedure commences as shown in FIG. 3 by removing the implant complete with cement and the fibrous tissue by first fitting a bone plug 30 and guide wire 31. Bone chips 32 are now added and compressed using an impactor or ram 33. The bone chips are built up layer by layer in the manner described in U.S. Pat. No. 5,665,121 and a stem phantom 34 is then introduced as shown in FIG. 5 to readily compress the bone chips and form a cavity 35 which is most clearly shown in FIG. 6.

Although in the present description a technique as set forth in U.S. Pat. No. 5,665,121 is described the invention can equally be applied to a newly made cavity in a femur.

The cavity 35 is now filled with cement 36, as shown in FIG. 6, and this may be pressurized if desired. A cannulated phantom 50 having a bore 49 is now introduced into the opening 35, as shown in FIG. 7, the insert portion or stem 51 having dimensions which are identical with or larger than those of a prosthesis which is intended to be fitted. The guide wire 31 provides means for accurately locating the phantom 50 in place. Unwanted cement from the filling 36 spills out as indicated by the arrows S.

Figure 11:
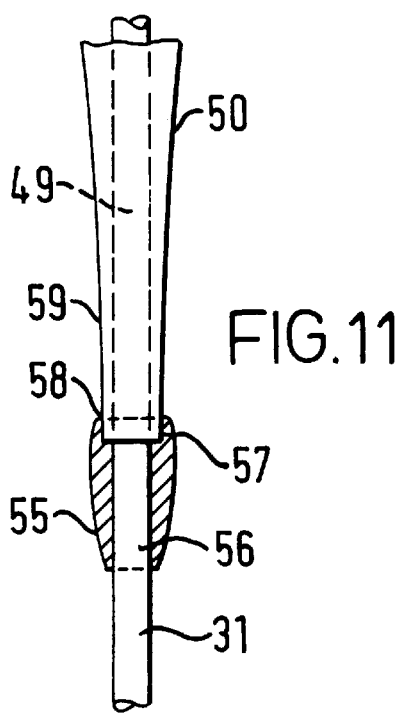
FIG. 11 is an enlarged view of part of FIG. 7 showing the present invention.
Figure 12:
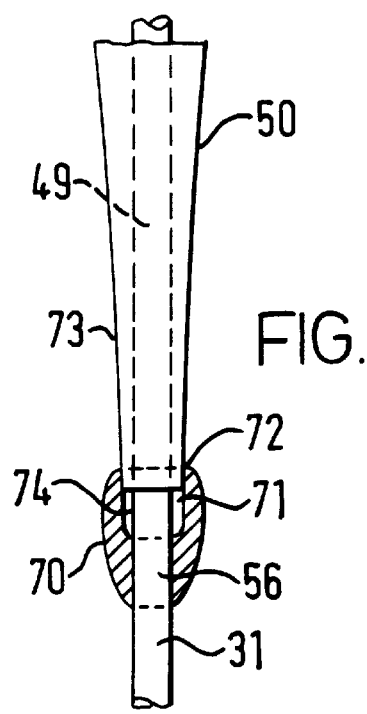
FIG. 12 is a similar view to FIG. 11 of an alternative embodiment.
Figure 13:
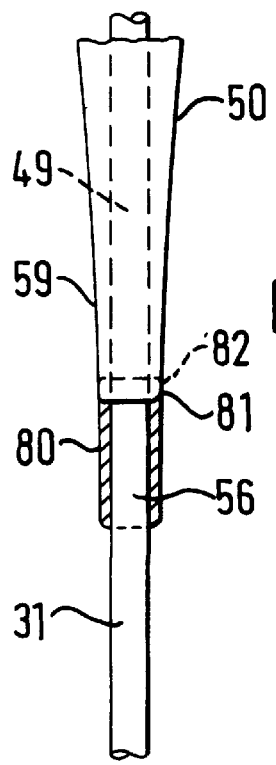
FIG. 13 is a side view of FIGS. 11 and 12 of another alternative embodiment.

FIG. 7 also shows the present invention which comprises a prosthetic implant cement deflector 55 which is shown more clearly in FIGS. 11 to 13. Prior to placing the phantom 50 on the guide wire 31 the cement deflector 55 is placed on the wire. It is then engaged on the distal tip of the phantom and moves down the guide wire 31 with it when the phantom is introduced into the opening. Because of the material from which the deflector is made it acts to seal the interface between the wire 31 and the surface of the bore 42 in the phantom. The deflector 55 can however slide down the wire 31. As it approaches the distal end of the opening the phantom causes a recess which is not shown in FIG. 7 because the phantom is, in that Figure, being introduced.

Once the cement is cured or in a suitable state the phantom 50 is withdrawn from the cavity leaving the cement deflector 55 in place and forming a lining of cement 37 as shown in FIG. 8. Because the deflector has acted to prevent cement from entering the interface between the wire 31 and the bore 49 the phantom can be withdrawn without difficulty. To further assist withdrawal the phantom 50 will generally have a polished surface or alternatively be coated with a material which does not adhere to the curing bone cement and it cannot have any retrograde features such as surface roughening which would inhibit withdrawal. The guide wire is now unthreaded from the intramedullary plug 30 and withdrawn through the deflector leaving the cavity lined with cement 37. The surgeon may now physically examine the cement cavity formed identifying whether there are specific areas where the cement mantle is incomplete or identifying other defects.

The surgeon now has two choices. If the mantle 36 as formed is entirely adequate he may use this for the fixation of the eventual implant component which is identified by reference numeral 38 in FIG. 8. The length of the stem of the prosthesis is arranged so that a void 60 is provided between the proximal end of the deflector 55 and the distal end 61 of the prosthesis 38. This void allows the prosthesis 38 to sink further into the cement as required and as is well known when using stems of this type.

In an alternative construction the deflector 55 can be formed so that it provides a void in its construction and into which the prosthesis 38 can sink. This construction is shown in more detail in FIG. 12.

If the cement mantle has defects however a further quantity of cement 39 is introduced into the cement cavity already formed as shown in FIG. 9, so as to fill any defects, and then an alternative prosthesis is introduced as shown in FIG. 10. This prosthesis 40 has an insert portion 41 which is of smaller size than the inset portion 51 of the phantom 50. Thus this is used as the final implantation.

With this technique a cement deflector can again be used on the phantom prosthesis in the method described above but if desired the prosthesis 40 with its smaller size insertion portion 41 can be provided with a centralizer 70 which is shaped to provide a void to accommodate subsequent downward movement and which is inserted with the prosthesis.

The use of this technique is dependent upon the form of an ultimate implant to be cemented into the cavity, since the phantom may not have any retrograde features that result in it being locked into the cement.

The stem geometry must allow an appropriate mechanism for the transmission of the load between the stem and the cement mantle so formed and an ideal hip stem for the use of this technique is the Exeter Hip Stem as sold by Howmedica International. This type of stem incorporates a double tapered and polished stem form which effectively engages the cement mantle causing principally compressive transmission of load from the stem to the cement and thereby to the bone.

This selection is important if the surgeon chooses to use the original cement mantle formed by the phantom 50 with the definitive implanted stem. Inevitably manufacturing variations will result in a marginal mismatch between the mantle and the definitive stem. The use of the double tapered stem which allow tapered re-engagement to occur with the relative compliant and visco-elastic cement at body temperature results in the effective taper load transmission despite the manufacturing differences.

With existing techniques there can be inappropriate positioning of an implant within the cavity in the bone and they do not result in a uniform control thickness of cement mantle which would give a better mechanical performance of the cement. This is a particular advantage of the new method of insertion.

This method can also be used with a cannulated system of broaches for shaping the opening. They can be used to form a known cavity shape over and above the nominal size of the implant and further guarantees the mantle geometry.

A system of depth indicators can be used for example as shown in the technique described is U.S. Pat. No. 5,192,283 and the depth indication system could also be used to position the phantom insert within the cavity formed by such broaches.

FIG. 11 shows one example of the present invention in more detail and which is for use as shown in FIGS. 7, 8, 9 and 10. The cement deflector 55 is made from polymethylmethacrylate (PMMA) and is provided with a central bore 56 which is dimensioned to be a sliding fit on the guide wire 31. The proximal end 57 of the deflector is recessed at the 58 to provide a push fit onto the distal end 59 of the phantom prosthesis 50.

It will be appreciated that, although the description relates to a phantom prosthesis, the invention can be performed on a surgical prosthesis which utilized a guide wire.

The primary advantage of the invention is that when the phantom prosthesis or prosthesis is moved down the guide wire 31 the cement deflector 55 acts to prevent cement passing into the guide bore 60 of the prosthesis around the guide wire 31. If the technique described with regard to FIGS. 2 to 10 is employed and a phantom prosthesis is used, if cement passes up the guide wire 31 into the bore 60 of the prosthesis and the phantom prosthesis is left in the opening until the cement part solidifies it can be difficult to withdraw the phantom prosthesis up the guide wire due to the ingress of cement. The cement deflector of the present invention prevents this happening.

FIG. 12 shows an alternative embodiment in which the same reference numerals are used to define similar parts but in this embodiment the deflector 70 is provided with an extended recess 71 the proximal end 72 of which is shaped and adapted to engage the distal end 73 of the phantom 50. This construction is designed so that when a non-cannulated prosthesis 40, similar to that shown in FIG. 1, is employed its distal end can extend into the proximal end 72 of the recess of the deflector 70 and a void 74 is provided by the lower part of the recess 71 into which the prosthesis 40 can subsequently sink. Thus, this construction, as shown in FIG. 12 can be used to replace the construction shown in FIG. 11 when used in the surgery described with regards to FIGS. 9 and 10 and overcomes the requirement for a centralizer 70.

FIG. 13 shows another alternative embodiment in which the same reference numerals are used to indicate similar parts to those shown in FIG. 11. In this construction however the cement deflector 80 has an external diameter which is substantially the same as the external diameter of the distal end 59 of the phantom prosthesis 50. The distal end of the phantom prosthesis is recessed as indicated by reference numeral 81 and receives a flange 82 formed on the end of the deflector. Thus, with this construction the deflector is held in place by the flange 82 during insertion and acts in a similar manner to the inserter described and shown in FIG. 11.

Figure 14:
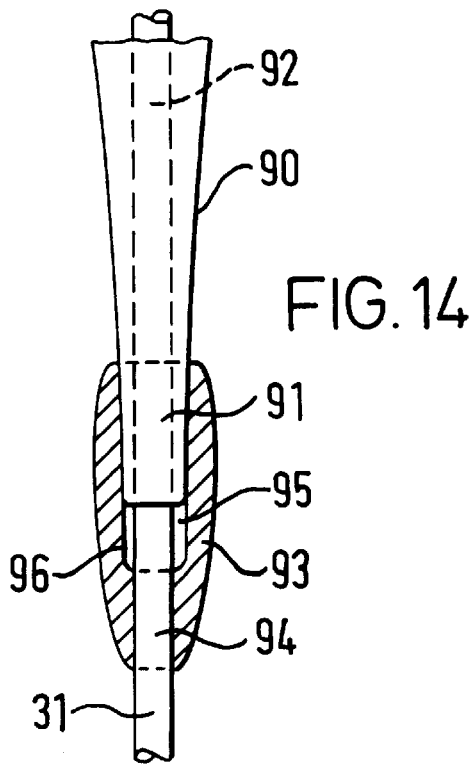
FIG. 14 shows an embodiment for use on a cannulated prosthesis.

FIG. 14 shows an embodiment of cement deflector which can be used with a cannulated prosthesis. The same reference numerals are again used to describe similar parts to those shown in the previous Figures. In this construction the cannulated prosthesis is indicated by reference numeral 90. The prosthesis has a distal end 91 and a bore 92 to receive the guide wire 31. A cement deflector 93 is employed which has a bore 94 to receive the guide wire 31 and an enlarged bore 95 which is dimensioned to receive the distal end of the prosthesis 90.

In use the cement deflector operates in a similar way to that described with regard to the other examples when they are employed on a cannulated phantom. This embodiment can be used either on the insertion into a newly prepared cavity in a bone or when used for replacement surgery.

The proximal portion of the enlarged bore 95 provides a void 96 in which the prosthesis 90 can subsequently sink. Once the prosthesis has been placed in position and the cement has set the guide wire 31 is of course removed but the cement deflector will once again have acted to prevent cement entering the interface between the wall of the bore 92 and the wire 31 thus allowing removal of the guide wire 31 without the usual difficulties.

What is claimed is:

1. A method of replacing a previously implanted femoral component in a hip medullary canal comprising:

removing the previously implanted femoral component;

placing a guide wire in the canal;

placing a bone plug on the guide wire and inserting the plug into a distal part of the canal;

placing bone chips into the canal and compacting the chips against the wall of the canal with an impactor to form a cavity;

placing a cement deflector at a distal tip of a cannulated prosthesis phantom or trial prosthesis;

placing bone cement in said cavity;

inserting said prosthesis phantom or trial prosthesis over the guide wire into said cement filled cavity;

allowing said cement to cure; and removing said guide wire from said cavity.

2. The method as set forth in claim 1 further including pressurizing the cement during curing.

3. The method as set forth in claim 2, wherein the pressurizing takes place after the trial or phantom is inserted.

4. The method as set forth in claim 1, wherein the cement deflector can seal an interface between the guide wire and the distal tip.

5. The method as set forth in claim 1 in which said cement deflector element has an external profile which is greater than the external dimensions of the distal tip of the trial phantom or prosthesis with which it is to be used.

6. The method as set forth in claim 5, wherein the deflector has a proximally facing opening for receiving the distal tip.

7. The method as set forth in claim 1, wherein the bone plug is placed on the guide wire before placing the guide wire in the canal.

8. The method as set forth in claim 1, wherein the cement deflector has an external diameter substantially the same as an external diameter of the trial or phantom prosthesis.

9. The method as set forth in claim 1 further including sealing a cannulation opening at the distal tip of the trial prosthesis or phantom by providing a cement deflector with a cannulation which seals around the guide wire and an opening which seals around the distal tip.

10. A prosthetic implant cement deflector system for use in prosthetic surgery when comprising employing a cannulated phantom or trial prosthesis or a cannulated prosthesis having a bore extending along a longitudinal axis receiving a guide wire, said bore extending through the prosthesis and forming an opening at a distal tip of the prosthesis and a cement deflector element having a bore with a sliding fit on said guide wire and having a proximal end surrounding said opening in the prosthesis, said element acting to seal an interface between the guide wire and the opening at the distal tip of the prosthesis.

11. A prosthetic implant cement deflector as claimed in claim 10 in which said deflector element is secured to a distal end of said prosthesis proximal to said distal tip.

12. A prosthetic implant cement deflector as claimed in claim 10 in which said element surrounds at least part of said distal tip of said prosthesis.

13. A prosthetic implant cement deflector as claimed in claim 12 in which said cement deflector element has a transverse external dimension greater than a transverse external dimension of the phantom or prosthesis distal tip.

14. A prosthetic implant cement deflector as claimed in claim 10 in which said cement deflector element is formed with a recess which is adapted to receive the distal end of a prosthesis with which it is to be used, said recess being dimensioned to extend beyond the end of the prosthesis to provide a void distal to the stem tip.

15. The prosthetic implant cement deflector as set forth in claim 10, wherein the deflector element has a recess sized to receive and surround the distal tip of said prosthesis.

16. The prosthetic implant cement deflector as set forth in claim 10, wherein the cement deflector element is made from a synthetic plastic material.

17. The prosthetic implant cement deflector as set forth in claim 16, wherein the plastic is polymethylmethacrylate.

\* \* \* \* \*

UNITED STATES PATENT AND TRADEMARK OFFICE
CERTIFICATE OF CORRECTION

PATENT NO. : 6,217,583 B1
DATED : April 17, 2001
INVENTOR(S) : Storer

It is certified that error appears in the above-identified patent and that said Letters Patent is hereby corrected as shown below:

<u>Title page, Item [54] and Column 1, line 2,</u>
Cancel "SYSTEM".

<u>Column 6,</u>
Line 17, cancel "when".
Line 17, cancel "employing".
Line 21, after "prosthesis" insert -- ; --.

Signed and Sealed this

Second Day of September, 2003

JAMES E. ROGAN
*Director of the United States Patent and Trademark Office*